(12) United States Patent
Orczy-Timko et al.

(10) Patent No.: US 10,582,966 B2
(45) Date of Patent: Mar. 10, 2020

(54) ARTHROSCOPIC DEVICES AND METHODS

(71) Applicant: RELIGN Corporation, Cupertino, CA (US)

(72) Inventors: Benedek Orczy-Timko, Budapest (HU); Aaron Germain, San Jose, CA (US)

(73) Assignee: RELIGN Corporation, Campbell, CA (US)

( * ) Notice: Subject to any disclaimer, the term of this patent is extended or adjusted under 35 U.S.C. 154(b) by 471 days.

(21) Appl. No.: 15/599,372

(22) Filed: May 18, 2017

(65) Prior Publication Data

US 2017/0252099 A1   Sep. 7, 2017

Related U.S. Application Data

(62) Division of application No. 15/096,546, filed on Apr. 12, 2016, now Pat. No. 9,681,913.

(60) Provisional application No. 62/150,758, filed on Apr. 21, 2015.

(51) Int. Cl.
*A61B 18/14* (2006.01)
*A61B 17/32* (2006.01)
*A61B 18/12* (2006.01)
*A61B 17/00* (2006.01)
*A61B 18/00* (2006.01)

(52) U.S. Cl.
CPC .......... *A61B 18/1482* (2013.01); *A61B 17/32* (2013.01); *A61B 17/32002* (2013.01); *A61B 18/1206* (2013.01); *A61B 18/14* (2013.01); *A61B 2017/00022* (2013.01); *A61B 2018/00565* (2013.01); *A61B 2018/00595* (2013.01); *A61B 2018/00601* (2013.01); *A61B 2018/00607* (2013.01); *A61B 2018/00958* (2013.01); *A61B 2018/1452* (2013.01); *A61B 2218/002* (2013.01); *A61B 2218/007* (2013.01)

(58) Field of Classification Search
None
See application file for complete search history.

(56) References Cited

U.S. PATENT DOCUMENTS

| 2,513,564 A | 7/1950 | Ingwersen |
| 2,514,545 A | 7/1950 | Ingwersen |
| 2,625,625 A | 1/1953 | Ingwersen |
| 2,689,895 A | 9/1954 | Ingwersen |

(Continued)

FOREIGN PATENT DOCUMENTS

| DE | 102005059864 A1 | 6/2007 |
| EP | 1034747 A1 | 9/2000 |

(Continued)

OTHER PUBLICATIONS

European Search Report dated Nov. 2, 2009 for EP Application No. 01967968.7.

(Continued)

*Primary Examiner* — Luther Behringer
(74) *Attorney, Agent, or Firm* — Wilson Sonsini Goodrich & Rosati

(57) ABSTRACT

An elongated shaft assembly includes a rotatable inner cutting sleeve and a non-rotating outer sleeve. A window of the inner cutting sleeve is selectively rotatable within an opening of the non-rotating outer sleeve to cut tissue with a sharpened cutting blade when rotated in a first rotational direction and to cut tissue with an electrode when rotated in a second rotational direction.

15 Claims, 6 Drawing Sheets

(56) References Cited

U.S. PATENT DOCUMENTS

| | | | |
|---|---|---|---|
| 3,611,023 A | 10/1971 | Souza, Jr. et al. |
| 3,838,242 A | 9/1974 | Goucher |
| 3,848,211 A | 11/1974 | Russell |
| 3,868,614 A | 2/1975 | Riendeau |
| 3,903,891 A | 9/1975 | Brayshaw |
| 4,060,088 A | 11/1977 | Morrison, Jr. et al. |
| 4,272,687 A | 6/1981 | Borkan |
| 4,781,175 A | 11/1988 | McGreevy et al. |
| 4,895,146 A | 1/1990 | Draenert |
| 4,977,346 A | 12/1990 | Gibson et al. |
| 5,012,495 A | 4/1991 | Munroe et al. |
| 5,122,138 A | 6/1992 | Manwaring |
| 5,207,675 A | 5/1993 | Canady |
| 5,256,138 A | 10/1993 | Burek et al. |
| 5,281,217 A | 1/1994 | Edwards et al. |
| 5,449,356 A | 9/1995 | Walbrink et al. |
| 5,490,854 A | 2/1996 | Fisher et al. |
| 5,641,251 A | 6/1997 | Leins et al. |
| 5,669,907 A | 9/1997 | Platt, Jr. et al. |
| 5,683,366 A | 11/1997 | Eggers et al. |
| 5,720,745 A | 2/1998 | Farin et al. |
| 5,759,185 A | 6/1998 | Grinberg |
| 5,766,195 A | 6/1998 | Nobles |
| 5,776,092 A | 7/1998 | Farin et al. |
| 5,810,809 A | 9/1998 | Rydell |
| 5,823,971 A | 10/1998 | Robinson et al. |
| 5,839,897 A | 11/1998 | Bordes |
| 5,849,010 A | 12/1998 | Wurzer et al. |
| 5,857,995 A | 1/1999 | Thomas et al. |
| 5,873,855 A | 2/1999 | Eggers et al. |
| 5,888,198 A | 3/1999 | Eggers et al. |
| 5,891,095 A | 4/1999 | Eggers et al. |
| 5,904,681 A | 5/1999 | West, Jr. |
| 5,913,867 A | 6/1999 | Dion |
| 5,964,752 A | 10/1999 | Stone |
| 5,989,248 A | 11/1999 | Tu et al. |
| 6,013,075 A | 1/2000 | Avramenko et al. |
| 6,013,076 A | 1/2000 | Goble et al. |
| 6,024,733 A | 2/2000 | Eggers et al. |
| 6,032,674 A | 3/2000 | Eggers et al. |
| 6,039,736 A | 3/2000 | Platt, Jr. |
| 6,056,747 A | 5/2000 | Saadat et al. |
| 6,066,134 A | 5/2000 | Eggers et al. |
| 6,099,523 A | 8/2000 | Kim et al. |
| 6,142,992 A | 11/2000 | Cheng et al. |
| 6,149,620 A | 11/2000 | Baker et al. |
| 6,159,208 A | 12/2000 | Hovda et al. |
| 6,225,883 B1 | 5/2001 | Wellner et al. |
| 6,235,020 B1 | 5/2001 | Cheng et al. |
| 6,238,391 B1 | 5/2001 | Olsen et al. |
| 6,261,241 B1 | 7/2001 | Burbank et al. |
| 6,296,636 B1 | 10/2001 | Cheng et al. |
| 6,332,886 B1 | 12/2001 | Green et al. |
| 6,348,051 B1 | 2/2002 | Farin et al. |
| 6,394,956 B1 | 5/2002 | Chandrasekaran et al. |
| 6,413,256 B1 | 7/2002 | Truckai et al. |
| 6,419,674 B1 | 7/2002 | Bowser et al. |
| 6,443,948 B1 | 9/2002 | Suslov |
| 6,475,215 B1 | 11/2002 | Tanrisever |
| 6,538,549 B1 | 3/2003 | Renne et al. |
| 6,579,289 B2 | 6/2003 | Schnitzler |
| 6,610,059 B1 | 8/2003 | West et al. |
| 6,632,220 B1 | 10/2003 | Eggers et al. |
| 6,656,195 B2 | 12/2003 | Peters et al. |
| 6,669,694 B2 | 12/2003 | Shadduck |
| 6,720,856 B1 | 4/2004 | Pellon et al. |
| 6,780,178 B2 | 8/2004 | Palanker et al. |
| 6,783,533 B2 | 8/2004 | Green et al. |
| 6,821,275 B2 | 11/2004 | Truckai et al. |
| 6,837,884 B2 | 1/2005 | Woloszko |
| 6,890,332 B2 | 5/2005 | Truckai et al. |
| 6,902,564 B2 | 6/2005 | Morgan et al. |
| 6,979,332 B2 | 12/2005 | Adams |
| 7,087,054 B2 | 8/2006 | Truckai et al. |
| 7,150,747 B1 | 12/2006 | McDonald et al. |
| 7,220,261 B2 | 5/2007 | Truckai et al. |
| 7,309,849 B2 | 12/2007 | Truckai et al. |
| 7,549,989 B2 | 6/2009 | Morgan et al. |
| 7,674,263 B2 | 3/2010 | Ryan |
| 7,678,069 B1 | 3/2010 | Baker et al. |
| 7,713,269 B2 | 5/2010 | Auge, II et al. |
| 7,717,710 B2 | 5/2010 | Danger et al. |
| 7,744,595 B2 | 6/2010 | Truckai et al. |
| 7,771,422 B2 | 8/2010 | Auge, II et al. |
| 7,819,861 B2 | 10/2010 | Auge, II et al. |
| 7,819,864 B2 | 10/2010 | Morgan et al. |
| 7,955,331 B2 | 6/2011 | Truckai et al. |
| 8,012,153 B2 | 9/2011 | Woloszko et al. |
| 8,016,823 B2 | 9/2011 | Shadduck |
| 8,062,319 B2 | 11/2011 | O'Quinn et al. |
| 8,075,555 B2 | 12/2011 | Truckai et al. |
| 8,192,424 B2 | 6/2012 | Woloszko |
| 8,192,428 B2 | 6/2012 | Truckai et al. |
| 8,221,404 B2 | 7/2012 | Truckai |
| 8,323,280 B2 | 12/2012 | Germain et al. |
| 8,333,763 B2 | 12/2012 | Truckai et al. |
| 9,179,923 B2 | 11/2015 | Gubellini et al. |
| 9,504,521 B2 | 11/2016 | Deutmeyer et al. |
| 9,585,675 B1 | 3/2017 | Germain et al. |
| 9,603,656 B1 | 3/2017 | Aaron et al. |
| 9,681,913 B2 | 6/2017 | Orczy-Timko et al. |
| 2003/0014051 A1 | 1/2003 | Woloszko |
| 2003/0083681 A1 | 5/2003 | Moutafis et al. |
| 2003/0125727 A1 | 7/2003 | Truckai et al. |
| 2003/0163135 A1 | 8/2003 | Hathaway |
| 2004/0044341 A1 | 3/2004 | Truckai et al. |
| 2004/0167427 A1 | 8/2004 | Quick et al. |
| 2005/0075630 A1 | 4/2005 | Truckai et al. |
| 2005/0228372 A1 | 10/2005 | Truckai et al. |
| 2006/0058782 A1 | 3/2006 | Truckai et al. |
| 2006/0074345 A1 | 4/2006 | Hibner |
| 2006/0178670 A1 | 8/2006 | Woloszko et al. |
| 2006/0200123 A1 | 9/2006 | Ryan |
| 2006/0224154 A1 | 10/2006 | Shadduck et al. |
| 2007/0213704 A1 | 9/2007 | Truckai et al. |
| 2008/0003255 A1 | 1/2008 | Kerr et al. |
| 2008/0103494 A1 | 5/2008 | Rioux et al. |
| 2008/0188848 A1 | 8/2008 | Deutmeyer et al. |
| 2008/0208249 A1 | 8/2008 | Blain et al. |
| 2009/0076498 A1 | 3/2009 | Saadat et al. |
| 2009/0270849 A1 | 10/2009 | Truckai et al. |
| 2010/0100091 A1 | 4/2010 | Truckai |
| 2010/0305565 A1 | 12/2010 | Truckai et al. |
| 2011/0282373 A1 | 11/2011 | Chekan et al. |
| 2012/0209112 A2 | 8/2012 | Patel et al. |
| 2012/0245580 A1 | 9/2012 | Germain et al. |
| 2012/0330292 A1 | 12/2012 | Shadduck et al. |
| 2013/0122461 A1 | 5/2013 | Shioiri |
| 2013/0172870 A1 | 7/2013 | Germain et al. |
| 2013/0267937 A1 | 10/2013 | Shadduck et al. |
| 2013/0296847 A1 | 11/2013 | Germain et al. |
| 2013/0296849 A1 | 11/2013 | Germain et al. |
| 2013/0317493 A1 | 11/2013 | Truckai et al. |
| 2013/0331833 A1 | 12/2013 | Bloom |
| 2014/0100567 A1 | 4/2014 | Edwards et al. |
| 2014/0336643 A1 | 11/2014 | Orczy-Timko et al. |
| 2017/0128083 A1 | 5/2017 | Germain et al. |
| 2017/0172648 A1 | 6/2017 | Germain et al. |
| 2017/0224368 A1 | 8/2017 | Germain et al. |

FOREIGN PATENT DOCUMENTS

| | | |
|---|---|---|
| WO | WO-0053112 A2 | 9/2000 |
| WO | WO-0062685 A1 | 10/2000 |
| WO | WO-0053112 A3 | 12/2000 |
| WO | WO-2007073867 A1 | 7/2007 |

OTHER PUBLICATIONS

International Search Report and Written Opinion dated Jul. 15, 2016 for International PCT Patent Application No. PCT/US2016/027157.
International Search Report and Written Opinion dated Mar. 8, 2017 for International PCT Patent Application No. PCT/US2016/058179.

(56) References Cited

OTHER PUBLICATIONS

International Search Report and Written Opinion dated May 16, 2017 for International PCT Patent Application No. PCT/US2017/016002.

International Search Report and Written Opinion dated May 23, 2012 for International PCT Patent Application No. PCT/US2012/023390.

International Search Report and Written Opinion dated Nov. 29, 2016 for International PCT Patent Application No. PCT/US2016/058145.

International Search Report dated Jan. 14, 2002 for International PCT Patent Application No. PCT/US2001/025409.

Kim, et al. Optical feedbacksignal for ultra short pulse ablation of tissue. Appl. Surface Sci. 1998; 127-129:857-862.

Notice of Allowance dated Jan. 6, 2017 for U.S. Appl. No. 14/960,084.

Notice of Allowance dated Feb. 8, 2017 for U.S. Appl. No. 14/977,256.

Notice of Allowance dated Feb. 16, 2017 for U.S. Appl. No. 15/096,546.

Notice of Allowance dated Dec. 2, 2016 for U.S. Appl. No. 14/977,256.

Notice of Allowance dated Dec. 30, 2016 for U.S. Appl. No. 14/977,256.

Office Action dated May 3, 2016 for U.S. Appl. No. 14/960,084.

Office Action dated Jul. 21, 2017 for U.S. Appl. No. 15/421,264.

Office Action dated Jul. 28, 2016 for U.S. Appl. No. 14/977,256.

Office Action dated Aug. 18, 2016 for U.S. Appl. No. 14/960,084.

Office Action dated Sep. 26, 2016 for U.S. Appl. No. 15/096,546.

Pedowitz, et al. Arthroscopic surgical tools: a source of metal particles and possible joint damage. Arthroscopy. Sep. 2013;29(9):1559-65. doi: 10.1016/j.arthro.2013.05.030. Epub Jul. 30, 2013.

Tucker et al. Histologic characteristics of electrosurgical injuries. J. Am. Assoc. Gyneco. Laproscopy. 1997; 4(2):857-862.

Volpato, et al., Application of Zirconia in Dentistry: Biological, Mechanical and Optical Considerations. Advances in ceramics-electric and magnetic ceramics, bioceramics, ceramics and environment. Sep. 2011.

ARTHROSCOPIC DEVICES AND METHODS

CROSS-REFERENCE TO RELATED APPLICATION

This application is a divisional of U.S. patent application Ser. No. 15/096,546, filed Apr. 12, 2016, now issued as U.S. Pat. No. 9,681,913, which claims the benefit of provisional application 62/150,758, filed on Apr. 21, 2015, the full disclosure of which is incorporated herein by reference.

BACKGROUND OF THE INVENTION

1. Field of the Invention

This invention relates to arthroscopic tissue cutting and removal devices by which anatomical tissues may be cut and removed from a joint or other site. More specifically, this invention relates to instruments configured for cutting and removing soft tissue and hard tissue with both mechanical cutting means and electrosurgical cutting means.

In several surgical procedures including subacromial decompression, anterior cruciate ligament reconstruction involving notchplasty, and arthroscopic resection of the acromioclavicular joint, there is a need for cutting and removal of soft tissues as well as bone. Currently, physicians use two or more arthroscopic devices to perform such a procedure. For example, a mechanical shaver may used to cut soft tissue while a high speed bone burr may be used to remove bone. In addition, one or more RF probes may also be used to cut certain types of tissue, to contour tissue surfaces, or to coagulate and seal tissue.

A typical arthroscopic shaver or burr comprises a metal cutting member carried at the distal end of a metal sleeve that rotates within an open-ended metal shaft. A suction pathway for removal of bone fragments or other tissues is provided through a window proximal to the metal cutting member that communicates with a lumen in the sleeve.

When metal shavers and burrs "wear" during a procedure, which can occur very rapidly when cutting bone, the wear can be accompanied by loss of micro-particles from fracture and particle release which occurs along with dulling due to metal deformation. In such surgical applications, even very small amounts of such foreign particles that are not recovered from a treatment site can lead to detrimental effects on the patient health, with inflammation being typical. In some cases, the foreign particles can result in joint failure due to osteolysis, a term used to define inflammation due to presence of such foreign particles. A recent article describing such foreign particle induced inflammation is Pedowitz, et al. (2013) Arthroscopic surgical tools: "A source of metal particles and possible joint damage", Arthroscopy—The Journal of Arthroscopic and Related Surgery, 29(9), 1559-1565. In addition to causing inflammation, the presence of metal particles in a joint or other treatment site can cause serious problems for future MRIs. Typically, the MRI images will be blurred by agitation of the metal particles caused by the magnetic field used in the imaging, making assessments of the treatment difficult.

Another problem with the currently available arthroscopic shavers is that mechanical cutting does not work well with some types of tissue. RF plasma-based electrosurgical cutting would be preferred, but reliable RF plasma shavers have not been developed.

Therefore, the need exists for arthroscopic shavers that can operate to cut and remove both soft tissue and bone tissue and further to remove bone tissue without the release of fractured particles and micro-particles into the treatment site. Further, there is a need for arthroscopic shavers that can use RF plasma for tissue resection. At least some of these objectives will be met by the inventions described below.

2. Description of the Background Art

Pedowitz, et al. (2013) Arthroscopic surgical tools: "A source of metal particles and possible joint damage", Arthroscopy—The Journal of Arthroscopic and Related Surgery, 29(9), 1559-1565 has been discussed above. Copending, commonly assigned U.S. patent application Ser. No. 14/960,084, filed on Dec. 4, 2015, and Ser. No. 14/977,256, filed on Dec. 21, 2015, the full disclosures of which are incorporated herein by reference, have disclosures related to the present application. See also U.S. Pat. Nos. 6,149,620 and 7,678,069.

SUMMARY OF THE INVENTION

In a first aspect of the present invention, a method for treating tissue comprises engaging a working end of a shaft assembly against a tissue interface. The working end includes an outer sleeve having a distal opening and an inner sleeve having a cutting window. A portion of the tissue interface is contacted by the inner sleeve's cutting window when exposed in the opening in the outer sleeve. The inner sleeve can be rotated in a first rotational direction relative to the outer sleeve to cut tissue engaged by a cutting edge on one side of the cutting window, typically by shearing with an opposed edge on the outer sleeve opening. The inner sleeve can be rotated in a first rotational direction relative to the outer sleeve to cut tissue extending through said windows as a cutting edge on one side of the inner cutting window passes through the tissue, typically by shearing with an opposed cutting edge on the distal opening. The inner sleeve can also be rotated in a second rotational direction opposite to the first rotational direction to cut tissue with an energized electrode disposed on or near (proximate) an opposite side of the cutting window of the inner sleeve.

In particular embodiments of the method of the present invention, the inner sleeve may be rotated in the first rotational direction to shear bone and other hard tissues and may be rotated in the second rotational to advance an energized electrode to cut soft tissue. Exemplary hard tissues include bone and the like, and exemplary soft tissues include muscle, nerve tissue, cartilage, meniscus, connective tissue, tendons, and ligaments, and the like. The tissue interface may be submerged in a liquid or a liquid may be directed at the tissue interface through a channel in the shaft assembly while engaging the working end and rotating the inner sleeve. Additionally, a negative pressure may be drawn through a passageway in the shaft assembly to remove cut tissue and other debris through the passageway.

In further embodiments of the methods of the present invention, a motor assembly may be detachably secured to the shaft assembly. The motor is configured to selectively rotate the inner sleeve or shaft in the first and second rotational directions. A radiofrequency (RF) power supply may also be detachably secured to the shaft assembly. The RF power supply is configured to selectively energize the electrode. A controller may be operatively attached to the motor and/or to the RF power supply. The controller may be configured to control the RF power supply to selectively deliver RF cutting current to the electrode when the motor rotates the inner sleeve in a cutting direction and to selectively not deliver cutting current to the electrode when the motor is not rotating the inner sleeve in the cutting direction.

Usually, a cutting current is delivered to the electrode only while the electrode is being rotated in a cutting direction. In a specific protocol, the cutting current is delivered to the electrode only during a selected arc of rotation of the inner sleeve. In an alternate protocol, the cutting current is delivered to the electrode during full rotation of the inner sleeve.

In still other embodiments of the methods of the present invention, the inner sleeve may be stopped in a selected rotational position relative to the outer sleeve to align the sleeve window of the inner sleeve with the opening in the outer sleeve in a selected orientation. The controller may be configured to deliver a coagulating current from the RF power supply to the electrode while the inner sleeve is stationary for coagulating tissue.

In a second aspect of the present invention, a surgical system comprises an outer sleeve having a longitudinal axis and an opening in a distal region thereof. An inner sleeve is rotationally disposed within said outer sleeve, and the inner sleeve has a distal region, a proximal region, and an interior passageway disposed therebetween. A cutting window is formed in a wall of the distal region of the inner sleeve, and a cutting edge is disposed on or along one side of the cutting window of the inner sleeve. An electrode is disposed on an opposite side of the cutting window of the inner sleeve so that rotating the inner sleeve in a first rotational direction relative to the outer sleeve cuts tissue with the cutting edge of the inner sleeve window and rotating the inner sleeve in a second rotational direction opposite to the first rotational direction cuts tissue engaged by the energized electrode.

In particular embodiments, the surgical systems of the present invention may further comprise a motor configured to selectively rotate in the inner sleeve in the first and second rotational directions. Said systems may still further comprise a radiofrequency (RF) current source configured to be coupled to the electrode, and often a controller operatively coupled to the motor and to the RF source.

The controller may be configured to selectively operate in a first mode in which the motor rotates the inner sleeve in the first rotational direction with the electrode not energized and in a second mode in which the motor rotates the inner sleeve in the second rotational direction with the RF source delivering an RF cutting or ablation current to the electrode to cut tissue. Optionally, the controller may be further configured to selectively operate in a third mode in which the inner sleeve is stopped in a selected position and the RF source delivers a cauterizing current to electrode which can be positioned in contact with tissue to coagulate targeted tissue. The controller may be further configured to selectively operate in a fourth mode in which the inner sleeve is stopped in a selected position and the RF source delivers a cutting or ablation current to the electrode which can be translated over tissue for surface ablation or contouring.

In still further options, the controller may be configured to selectively operate in a fifth mode in which the motor rotationally oscillates the inner sleeve relative to the outer sleeve in the first and second rotational directions. Further optionally, the controller may be configured to selectively operate in a sixth mode in which the motor drives the inner sleeve rotationally and contemporaneously drives (1) the inner sleeve axially relative to the outer sleeve or (2) an assembly of the inner and outer sleeves axially relative to a handle.

In other embodiments, the surgical systems of the present invention may include a hub or handle disposed at a proximal end of the shaft assembly. The motor may be detachably connected to the hub or handle, and a proximal portion of the shaft assembly may be configured to be connected to an external fluid source to deliver a fluid through a passageway in the shaft assembly and release the fluid from a distal region of the shaft assembly to a tissue interface. A proximal portion of the shaft assembly may be configured to be connected to an external vacuum source to draw a vacuum through a passageway in the shaft assembly to aspirate fluid from a tissue interface at a distal region of the shaft assembly.

In still other embodiments, at least the cutting edge of the inner sleeve comprises a ceramic. Often, the entire distal portion of the inner sleeve comprises the ceramic.

In other alternative embodiments, the controller may be configured to stop rotation of the inner sleeve in a selected rotational position relative to the outer sleeve. For example, the opening in the outer sleeve and the window in the inner sleeve may be rotationally aligned in the stopped position. Alternatively, the opening in the outer sleeve and the window in the inner sleeve may be out of rotational alignment in the stopped position.

In a third aspect of the present invention, a tissue treatment device comprises a shaft assembly having an outer shaft and an inner shaft co-axially received in the outer shaft. A hub or handle may be attached to a proximal end of the shaft assembly, and a motor may be attachable to the hub or handle. The motor may be configured to rotatably drive the inner sleeve relative to the outer sleeve, and a window and an opening may be formed in distal portions of the inner and outer sleeves, respectively. The inner opening includes a cutting blade along one axially aligned edge and an electrode along a second axially aligned edge.

In a fourth aspect of the present invention, an arthroscopic tissue treatment device comprises a shaft assembly having an outer shaft and an inner shaft received in a passageway of the outer shaft. The first and second shafts each have an opening formed in a distal portion thereof, and a hub may be attached to a proximal end of the shaft assembly. A motor may be attachable to the hub, and the motor is typically configured to rotatably drive the inner shaft in first and second rotational directions relative to the outer shaft. A cutting blade may be formed or otherwise disposed on one side of the opening of the inner sleeve, and an electrode may be formed or otherwise disposed on an opposed side of the opening of the inner sleeve. A coupler may be provided to couple the shaft assembly to a handle and couple the inner sleeve to the motor carried by the handle.

In a fifth aspect of the present invention, a tissue cutting instrument for differentially cutting tissue comprises an elongate shaft having a working end with a moveable cutting member. A motor drive and controller moves the cutting member, and the controller may be configured to move the cutting member in a first direction to mechanically cut tissue and in a second different direction to electrosurgically cut tissue.

In particular embodiments, the first and second directions of the tissue cutting instruments of the present invention are opposing rotational directions. The cutting member may mechanically cut tissue with a sharp edge and/or may electrosurgically cut tissue with a cutting electrode. The tissue cutting instruments may further comprise a negative pressure source communicating with a passageway in the cutting member for removing cut tissue from a treatment site. The tissue cutting instrument may still further comprise an RF source and controller operatively coupled to the electrode. Additionally, the controller of the tissue cutting instrument may be configured to energize the electrode only when the cutting member moves in the second direction.

The present invention further provides a high-speed cutter that is fabricated of a ceramic material that has a window with a first side having a sharp cutting edge for mechanical cutting and a second side with an electrode for RF plasma-based cutting. In one variation, the ceramic cutter is molded with sharp cutting edges and is adapted to be motor driven at speeds ranging from 3,000 rpm to 20,000 rpm. The ceramic cutting member is coupled to an elongate inner sleeve that is configured to rotate within a metal, ceramic or composite outer sleeve. While the cutting assembly and ceramic cutting member of the invention have been designed for arthroscopic procedures, such devices can be fabricated in various cross-sections and lengths and can be use in other procedures for cutting bone, cartilage and soft tissue such as in ENT procedures, spine and disc procedures and plastic surgeries.

In still other aspects, the present invention provides a medical device that includes an elongated sleeve having a longitudinal axis, a proximal end and a distal end. A cutting member extends distally from the distal end of the elongated sleeve, and has sharp cutting edges. The cutting head is formed from a wear-resistant ceramic material, and a motor coupled to the proximal end of elongated sleeve rotates the cutting member. The cutter may be engaged against bone and rotated to cut bone tissue without leaving any foreign particles in the site.

As used herein, the phrase "tissue interface" means a surface or exposed interior volume of a target tissue to be treated with the devices and methods of the present invention. The tissue may be a hard tissue, such as bone, or may be a soft tissue, such as muscle, nerve tissue, cartilage, meniscus, connective tissue, tendons, ligaments, and the like. The tissue interface may be present on a natural surface of a body structure, such as bone, cartilage, meniscus, connective tissue, tendons, or ligaments, or may be a surgically exposed tissue surface, such as surgically opened solid tissue. In exemplary procedures, the tissue surfaces will be accessed by minimally invasive surgical procedures, such as arthroscopy, laparoscopy, thoracoscopy, and the like.

As used herein, the phrase "a portion of the tissue interface," means a piece, segment, section, fragment, or the like of tissue interface to be cut or excised from the remaining volume of the tissue interface by the apparatus and methods of the present invention.

As used herein, the phrase "a portion of the tissue interface engaged by a/the cutting window," means pressing or otherwise contacting a working end of the tissue resection apparatus of the present invention against the tissue interface which will cut hard tissue as a burr or will cut soft tissue by causing a portion of tissue from the tissue interface to be received in the aperture or opening which is created in the working end when the inner and outer cutting openings are at least partially rotationally aligned.

As used herein, the phrases "adapted to" and "configured to" perform a function mean that the structure of the device, apparatus, or components thereof is such that the device, apparatus, or components will necessarily be able to perform the specified function as performed by the exemplary structures described in the specification herein.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope

DETAILED DESCRIPTION OF THE INVENTION

The systems and methods of the present invention are illustrated and described herein by means of a surgical system that is adapted for use in performing arthroscopic procedures or other similar procedures, for example to remove, cut, trim, remodel, reshape or modify soft and hard tissues in a patient's shoulder, knee, hip or other joint. The surgical system 100 and cutting device or shaver assembly 102 (FIG. 1) is particularly suitable for performing procedures in a patient's joint that requires resection of soft tissue as well as the cutting or modification of bone. The system and methods of the present invention are not limited to arthroscopy, and can further be used in endoscopic and laparoscopic procedures as well as open surgeries and robotic surgical procedures.

Figure 1:
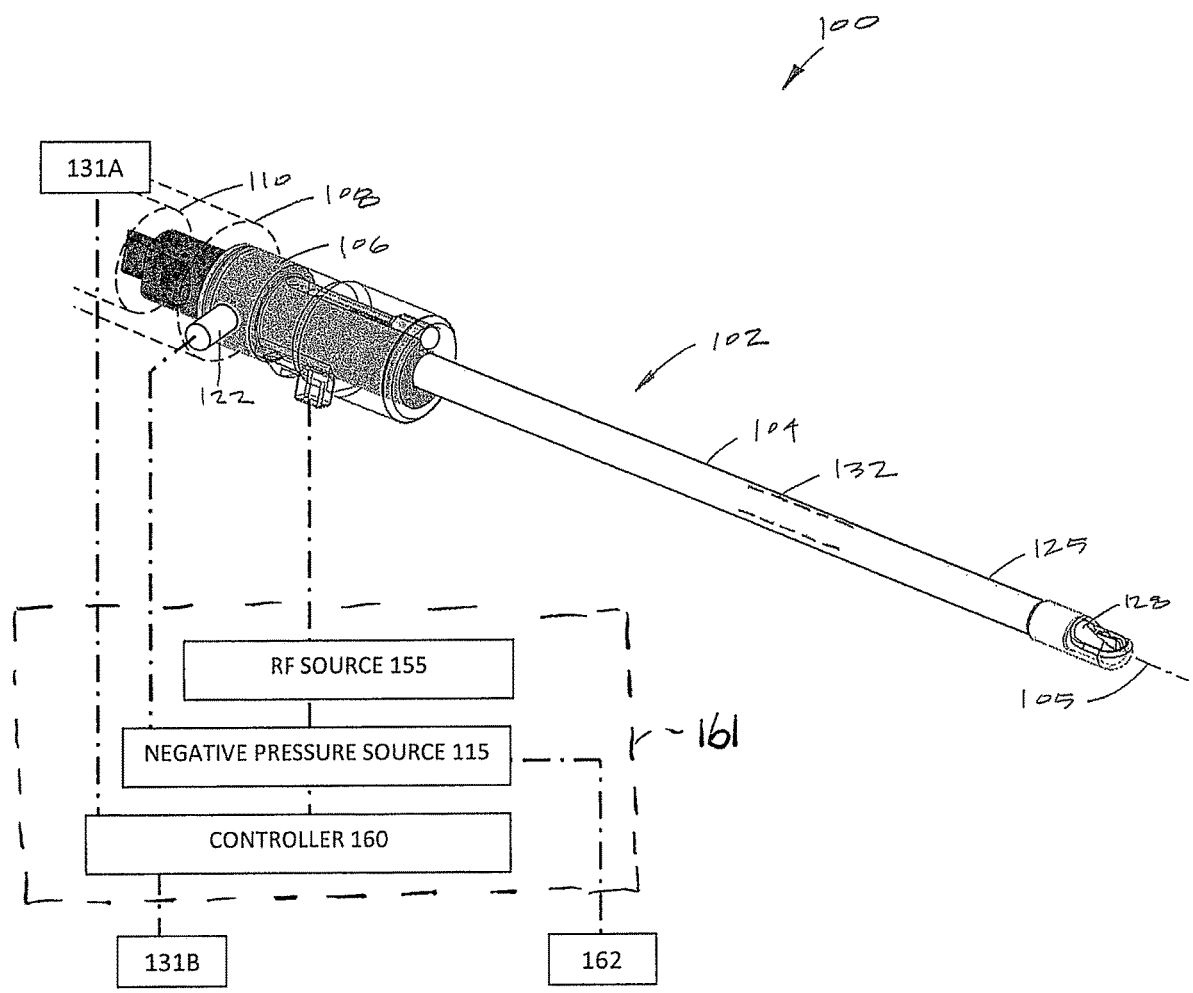
FIG. 1 is a perspective view of an arthroscopic cutting system according to one exemplary variation.

FIG. 1 illustrates one variation of a surgical system 100 and arthroscopic cutting device or shaver assembly 102 that is adapted to cut both hard and soft tissue and thereafter suction the tissue chips and debris through a passageway in the device to a collection reservoir. In a typical system, the cutting device 102 can be used in association with an independent fluid management system known in the art which provides for fluid inflows into a working space and for fluid outflows from the working space as well as pressure monitoring and control. In another variation described below, the surgical system 100 and cutting device 102 can have an integrated fluid management system.

In FIG. 1, it can be seen that the cutting device 102 has a shaft portion 104 that extends about longitudinal axis 105 and has a proximal hub 106 that can be detachably coupled to a non-disposable handle or hand piece 108 that carries a motor drive 110. As can be understood from FIGS. 1 and 2, the elongate shaft 104 comprises an outer tubular shaft or sleeve 125 and an inner tubular shaft or sleeve 128. The inner sleeve 128 is rotatably disposed in a bore 130 of the outer sleeve 125. The assembly of outer sleeve 125 and inner sleeve 128 can be of any suitable outer diameter, for example between 2 mm and 10 mm suited for typical arthroscopic procedures, and often would be from 3 mm to 6 mm in outer diameter.

The user can actuate a finger-operated actuator mechanism or a footswitch to cause the inner sleeve 128 to move or rotate within interior passageway 130 of outer sleeve 125. In one variation shown in FIG. 1, the hand piece 108 has an actuator mechanism 131A for sending activation signals and de-activation signals to a controller 160 to operate the motor drive 110. In a variation, the actuator mechanism can selectively activate the motor drive to rotate in either rotational direction relative to axis 105, or the actuator mechanism 131A can be operated to oscillate the inner sleeve a selected number of rotations in a first direction and then a selected number of rotations in the opposing direction. As will be described below, the system 100 also may have a footswitch 131B (or hand switch) for actuating an RF energy delivery function. Conveniently, the controller may be included in a common enclosure 161 together with the RF source 155 and/or the negative pressure source 115, where the enclosure may be configured to be mounted on a table or a mobile cart, optionally with a fluid source for delivering a fluid through the sleeve assembly.

In general, as is known in the art, a negative pressure source 115 (FIG. 1) is provided for suctioning fluid and cut tissue outwardly from the cutting device 102 through an interior passageway 132 in the inner sleeve 128. In this variation, the negative pressure source 115 is coupled to a passageway in the handle 108 as is known in the art, or the negative pressure source 115 can be coupled to a port 122 on hub 106 of the cutting device 102 (see FIG. 1).

Figure 2:
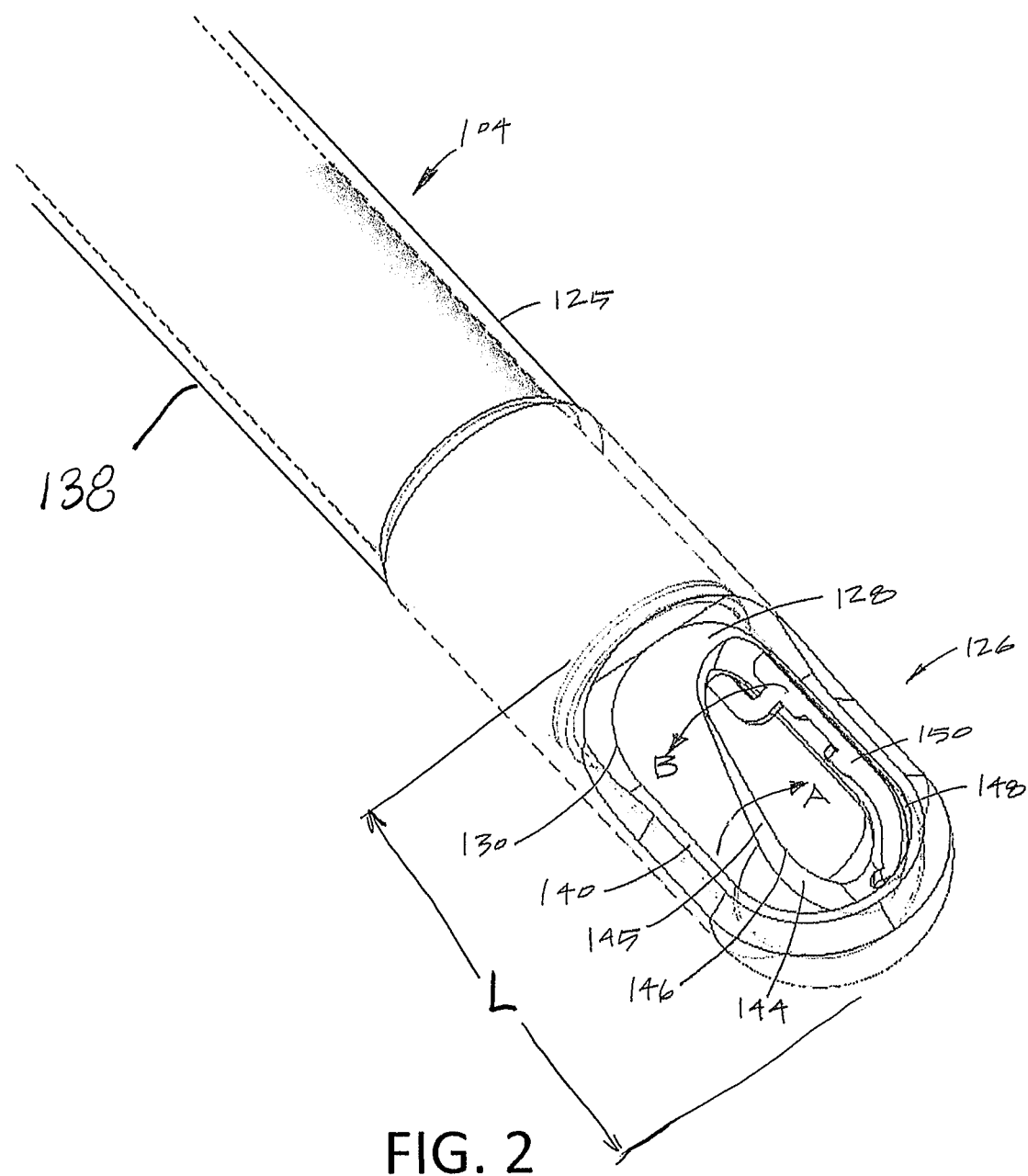
FIG. 2 is an enlarged perspective view of the working end of the cutting device of FIG. 1 showing windows or openings formed in an outer shaft and an movable inner shaft.

Referring to FIGS. 1 and 2, the outer sleeve 125 can be formed from one or more materials, such as stainless steel, ceramic, plastic or a combination thereof. In one variation, the outer sleeve 125 can be substantially rigid along its entire longitudinal length. In another variation, a sleeve portion proximal to window 140 can be flexible or articulated while an intermediate portion can be substantially rigid. The outer sleeve 125 can have a substantially uniform diameter as in the illustrated in FIG. 1. In another variation, a diameter of an outer sleeve 125 can decrease in the distal direction such that a distal working end of the outer sleeve 125 has a smaller diameter than a proximal portion thereof.

Figure 3A:
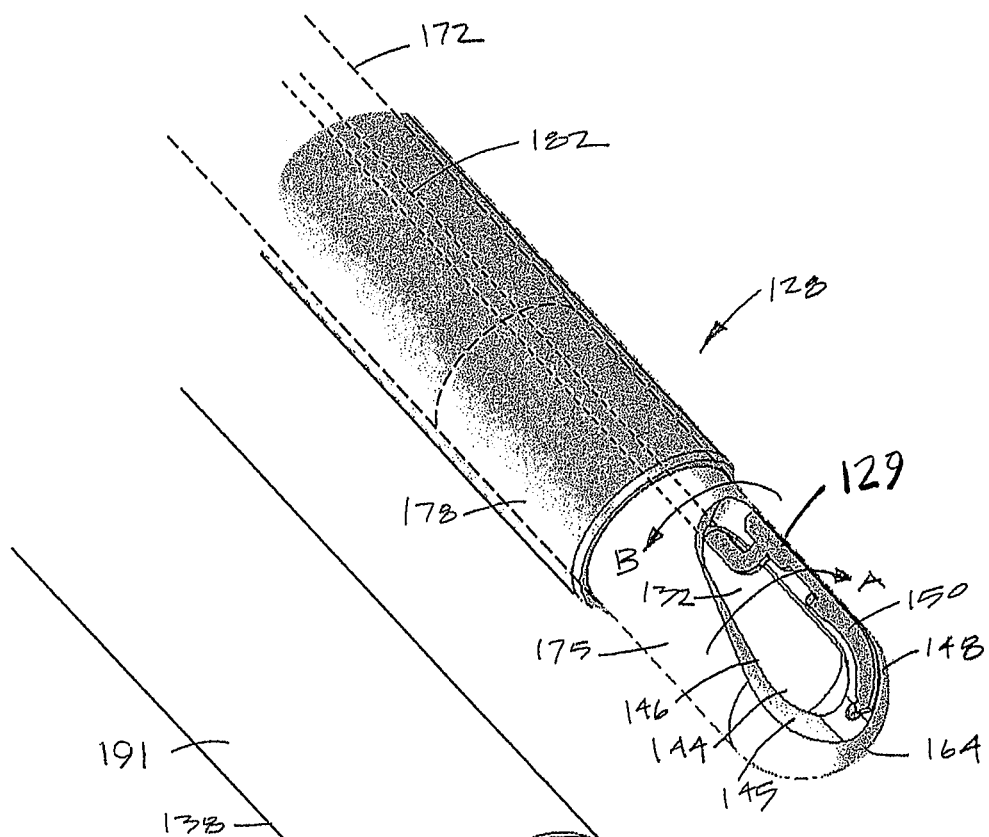
FIG. 3A is a perspective view of the distal end of inner shaft of FIG. 2 separated from the outer shaft.
Figure 3B:
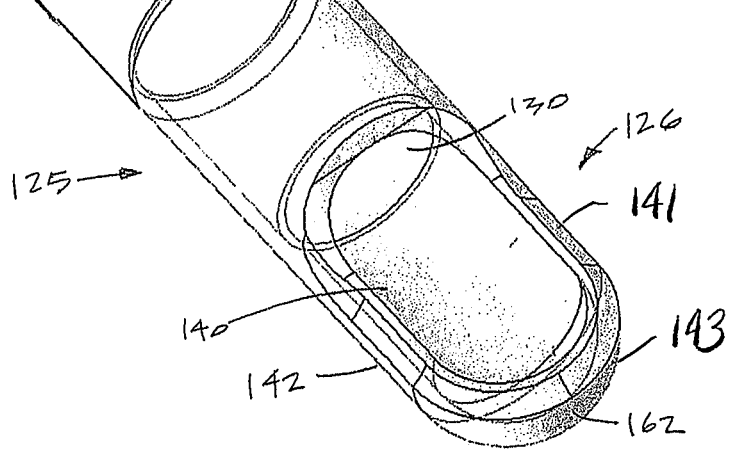
FIG. 3B is a perspective view of the outer shaft of FIG. 2 separated from the inner shaft.

In one variation shown in FIGS. 2 and 3B, the outer sleeve 125 has a metal extending portion or sleeve 138. An outer ceramic body 142 is coupled, usually fixedly attached, to a distal end of the metal sleeve 138 and has a window or opening 140 therein. The window or opening 140 can be formed in a sidewall 141 of the outer ceramic body 142, or the window 140 can be partly in the sidewall 141 and partly in a rounded distal end 143 of outer ceramic body 142 as is known in tubular arthroscopic cutters. In another variation, the window or opening 444 can comprise an open end of a working end 400B of an outer sleeve.

As can be seen in FIG. 3A, the inner sleeve 128 has an inner sleeve window 144 which may be elongated axially and may have a first cutting side 145 that comprises a first sharp cutting edge 146 and a second RF cutting side 148 that includes an electrode 150. FIG. 1 further shows that the cutting device 102 may be coupled to a radiofrequency (RF) source 155 and a controller 160 which are operatively connected to the electrode 150.

As can be understood from FIG. 3A, each of the first and second cutting sides 145 and 148 of inner sleeve window 144 are adapted for a differential means of cutting, depending on the direction of rotation of the sleeve 128 and thus which cutting side, 145 or 148, is the "leading edge" for interfacing with, or contacting, tissue when rotating. The sharp edge 146 is adapted for mechanically cutting tissue or bone when rotated at suitable speeds. The second cutting edge 148 of window 44 in inner sleeve 128 includes electrode 150 that is adapted for electrosurgically ablating or cutting tissue.

Referring to FIG. 2, the openings 140 and 144 in the outer and inner sleeves, respectively, are configured to receive tissue such that rotation of inner sleeve 128 relative to the outer sleeve 125 can cut, resect, reshape or modify tissue. In particular, the opening 144 in the inner sleeve 128 extends through an inner sleeve wall 129 and thus is in communication with the interior passageway 132 (FIG. 1) such that any cut or resected soft or hard tissue can be suctioned through the interior passageway 132 to a collection reservoir 162.

In the embodiment of FIGS. 2 and 3A, the outer sleeve 125 has a window 140 that extends approximately half-way (180°) around the outer ceramic body 142. The inner cutting sleeve 128 has an inner ceramic body 175 at a distal end thereof, and the inner ceramic body has a window 144 with a substantially oval or tear-drop shape and a length L in a proximal-distal direction that is greater than its width. It should be appreciated that the window 144 can have other shapes, such as rectangular, circular, square, trapezoidal, etc. By way of non-limiting example, the length L of the openings 140 and 144 in the outer and inner ceramic bodies, respectively, can be in a range of about 2 to 20 mm, for example, about 4 to 10 mm, depending on the diameter of the working end.

In the variation illustrated in FIG. 3A, the first sharp cutting edge 146 is formed on one side 145 of window 144 in the inner sleeve 128 and can be a straight edge, a serrated edge, a fluted edge, an abrasive edge or any suitable edge adapted for mechanically cutting tissue or bone. The first sharp cutting edge 146 extends generally in a proximal-distal direction alongside 145 of window 144 and comprises a leading edge when the inner sleeve 128 rotates in direction A indicated in FIGS. 2 and 3A.

Figures 4A, 4B:
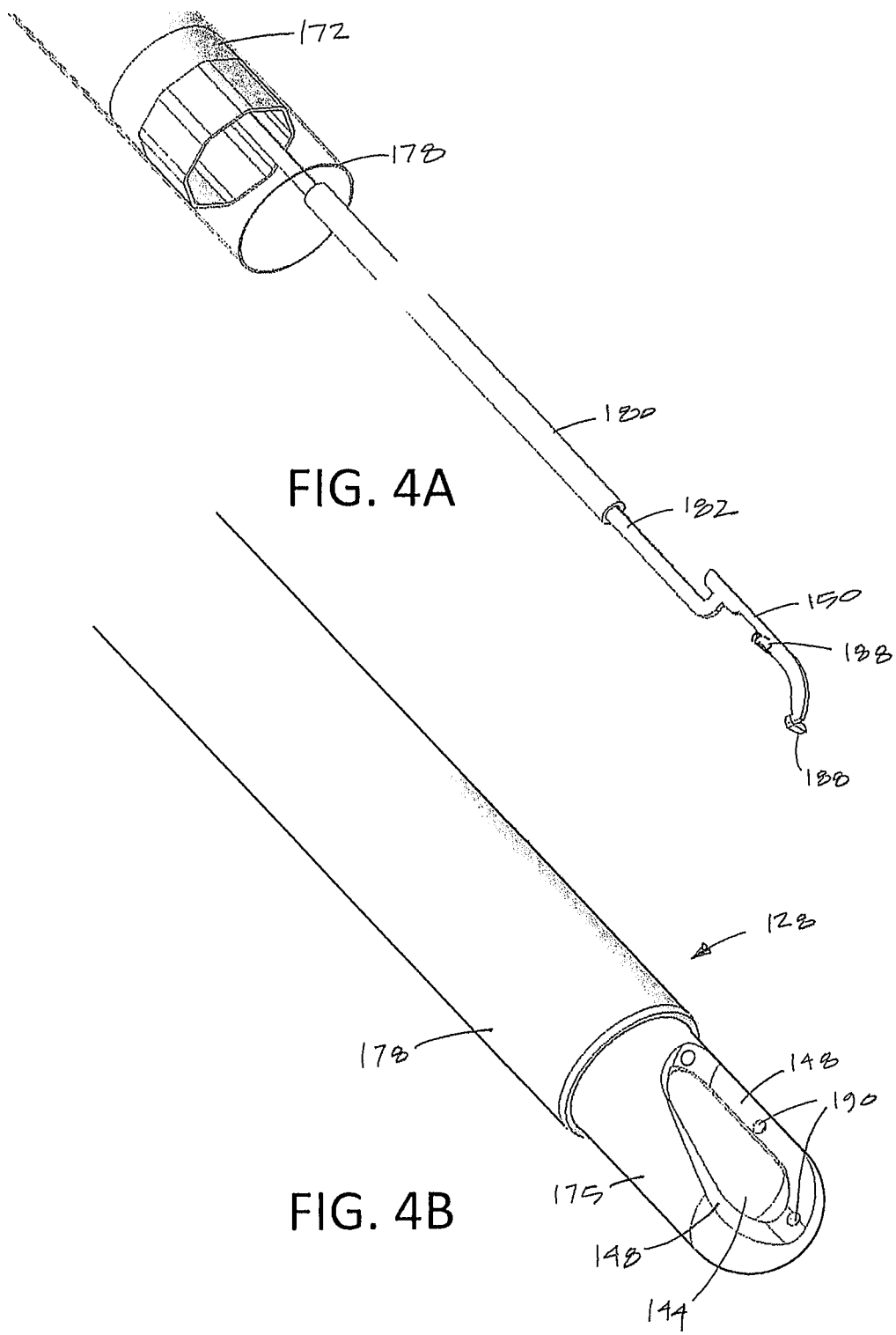
FIG. 4A is a perspective view of the electrode separated from the inner shaft of FIG. 4B.
FIG. 4B is a perspective view of the distal end of the inner shaft set to receive the electrode of FIG. 4A.

FIG. 3A further illustrates the second RF cutting edge 148 of inner sleeve window 144 in inner sleeve 128 which includes electrode 150. The electrode 150 comprises a suitable material electrode material, such as stainless steel or tungsten, and can be pre-formed to be coupled to the edge 148 of the window or near the edge of the window. The edge 148 and electrode 150 extend generally in a proximal-distal direction along the side of opening 144 and comprise a leading edge when the inner sleeve 128 rotates in direction B indicated in FIGS. 2 and 3A. Referring to FIG. 3A, the inner sleeve 128 can be formed from one or more materials, such as stainless steel, ceramic, plastic or a combination thereof. In the variation of FIG. 3A, the inner sleeve 128 has a stainless steel shaft portion 172 that is coupled to a distal ceramic body 175 of a wear-resistant ceramic material further described below that is configured with window 144. FIGS. 3A and 4A further shows an electrically insulating and lubricious polymer sleeve 178 covering the metal shaft portion 172 of inner sleeve 128.

Now referring to FIGS. 3A, 3B and 4B, the ceramic body 142 and ceramic body 175 comprise a monolith that is fabricated entirely of a technical ceramic material that has a very high hardness rating and a high fracture toughness rating, where "hardness" is measured on a Vickers scale and "fracture toughness" is measured in $MPam^{1/2}$. Fracture toughness refers to a property which describes the ability of a material containing a flaw or crack to resist further fracture and expresses a material's resistance to brittle fracture. The occurrence of flaws is not completely avoidable in the fabrication and processing of any components. The authors evaluated technical ceramic materials and tested prototypes to determine which types of ceramics are best suited for the ceramic body 175 with cutting edge 146 as disclosed in co-pending U.S. patent application Ser. No. 14/960,084, filed Dec. 4, 2015, which is incorporated herein by this reference.

In general, the technical ceramics disclosed herein have a hardness ranging from approximately 10 GPa to 15 GPa, which is five to six times greater than stainless steel. Such ceramics are 10 to 15 times harder than cortical bone. As a result, the sharp cutting edges of a ceramic remain sharp and will not become dull when cutting bone, compared to stainless steel. The fracture toughness of suitable ceramics ranges from about 5 MPam$^{1/2}$ to 13 MPam$^{1/2}$ which is sufficient to prevent any fracturing or chipping of the ceramic cutting edges. The authors determined that a hardness-to-fracture toughness ratio ("hardness-toughness ratio") is a useful term for characterizing ceramic materials that are suitable for the invention as can be understood form the TABLE A below, which compares the hardness and fracture toughness values of cortical bone and a 304 stainless steel with nine exemplary technical ceramic materials which are suitable for use in the present invention.

TABLE A

| | Hardness (GPa) | Fracture Toughness (MPam$^{1/2}$) | Ratio Hardness to Fracture Toughness |
|---|---|---|---|
| Cortical bone | 0.8 | 12 | 0.07:1 |
| Stainless steel 304 | 2.1 | 228 | 0.01:1 |
| Yttria-stabilized zirconia(YTZP) YTZP 2000 (Superior Technical Ceramics) | 12.5 | 10 | 1.25:1 |
| YTZP 4000 (Superior Technical Ceramics) | 12.5 | 10 | 1.25:1 |
| YTZP (CoorsTek) | 13.0 | 13 | 1.00:1 |
| Magnesia stabilized zirconia (MSZ) Dura-Z ® (Superior Technical Ceramics) | 12.0 | 11 | 1.09:1 |
| MSZ 200 (CoorsTek) | 11.7 | 12 | 0.98:1 |
| Zirconia toughened alumina (ZTA) YTA-14 (Superior Technical Ceramics) | 14.0 | 5 | 2.80:1 |
| ZTA (CoorsTek) | 14.8 | 6 | 2.47:1 |
| Ceria stabilized zirconia CSZ (Superior Technical Ceramics) | 11.7 | 12 | 0.98:1 |
| Silicon Nitride SiN (Superior Technical Ceramics) | 15.0 | 6 | 2.50:1 |

As can be seen in TABLE A, the hardness-toughness ratio for the listed ceramic materials ranges from 98-fold to 250-fold greater than the hardness-toughness ratio for stainless steel 304. In one aspect of the invention, a ceramic cutter for cutting hard tissue is provided that has a hardness-toughness ratio of at least 0.5:1, preferably at least 0.8:1, and more preferably at least 1:1.

In some embodiments, the outer and inner ceramic bodies 142 and 175 may comprise a form of zirconia of a type that has been used as dental implants. The technical details of such zirconia-based ceramics can be found in Volpato, et al., "Application of Zirconia in Dentistry: Biological, Mechanical and Optical Considerations", Chapter 17 in *Advances in Ceramics—Electric and Magnetic Ceramics, Bioceramics, Ceramics and Environment* (2011), the full disclosure of which is incorporated herein by reference. Such ceramics may be doped with stabilizers to increase the strength and fracture toughness for use in the present invention.

In a specific embodiment, the ceramic bodies 142 and/or 175 may be fabricated from an yttria-stabilized zirconia commercially available from CoorsTek Inc., 16000 Table Mountain Pkwy., Golden, Colo. 80403 or Superior Technical Ceramics Corp., 600 Industrial Park Rd., St. Albans City, Vt. 05478. Other suitable technical ceramics include magnesia-stabilized zirconia, ceria-stabilized zirconia, zirconia toughened alumina, and silicon nitride. In general, in one aspect of the invention, the ceramic bodies 142 and/or 175 may comprise monolithic or monoblock ceramic bodies having a hardness rating of at least 8 GPa (kg/mm$^2$). In another aspect of the invention, the ceramic bodies 142 and/or 175 may comprise monolithic or monoblock ceramic bodies having a fracture toughness of at least 4 MPam$^2$.

The ceramic bodies 142 and 175 may be fabricated by molding a ceramic powder, sintering and then heating the molded part at high temperatures over precise time intervals to transform the compressed ceramic powder into a ceramic monoblock in the target hardness range and fracture toughness range as described above. In one variation, the molded ceramic member part can be strengthened by isostatic pressing of the part. Following the ceramic fabrication process, a subsequent grinding process optionally may be used to sharpen and/or serrate the sharp cutting edge 146 of the inner ceramic body 175. Techniques for fabricating components comprising such monolithic or monoblock ceramics are known, but have not believed to have been previously been used in the field of arthroscopic or endoscopic electrosurgical cutting or resecting devices.

As can be seen in FIG. 4A, the electrode 150 has a shaft portion 182 that extends through the interior passageway 132 in sleeve 128 and has an electrically insulating coating 180 extending over the electrode's shaft portion 182 to prevent its contact with metal sleeve portion 172 (see FIGS. 3A and 4A).

FIGS. 4A-4B further illustrate an attachment pin 188 in the form of a projecting element on electrode 150. At least one such pin 188 is adapted to insert into a cooperating recess or bore 190 in the second RF cutting side 148 of window 144 in the inner ceramic body 175. The pin element(s) 188 can be press fit or fixed with an adhesive in the bores 190 to secure the electrode in place in the edge 148 of the window 144.

In the variation of FIGS. 2, 3A-3B, the electrode 150 can comprise an active electrode as known in the art for use in a submerged arthroscopic procedure and all or a portion of an outer surface 191 of the metal sleeve portion 138 of outer sleeve 125 can provide a return or dispersive electrode for connection to the RF source 155 (FIG. 1).

In general, a method for treating tissue in accordance with the principles of the present invention comprises introducing a working end of an elongated shaver assembly, such as the shaver assembly 102, into a tissue surface or other interface, rotating the inner sleeve 128 in a first rotational direction to cut tissue (soft tissue and bone) with the sharp edge 146 thereof and alternatively rotating the inner sleeve 128 in a second opposing rotational direction to cut tissue with the electrode 150 while delivering RF energy in the form of a cutting or ablation current to the electrode. Mechanical cutting with the sharp cutting edge 146 can be particularly effective or otherwise preferred for cutting hard tissue, such as bone, while RF cutting with the electrode can be particularly suitable or otherwise preferred for cutting soft tissue.

In certain embodiments, the tissue interface may be submerged in a liquid, for example saline. In other embodiments, saline or other liquids may be delivered through the shaver assembly to the tissue surface to flood the target resection region.

The method typically uses a motor (usually incorporated into the shaver assembly or handle) to rotate the inner sleeve 128 in the first and second rotational directions at various selected speeds ranging from 100 rpm to 50,000 rpm. In one variation, when the sharp ceramic cutting edge 146 is used to cut soft tissue, the speed range would be from 100 rpm to 10,000 rpm. When the sharp ceramic cutting edge 146 is used to cut bone, the speed range would be higher, for example, from 1,000 rpm to 25,000 rpm. When the edge 148 with electrode 150 is used to cut tissue, the speed range would be, for example, from 100 rpm to 10,000 rpm.

In general, the methods of the present invention may further includes applying negative pressure from source 115 to passageway 132 in the inner sleeve 128 to extract fluid and cut tissue.

Referring to FIG. 1, the controller 160 is configured to energize the electrode 150. For example, the controller may energize the electrode continuously while the inner sleeve 128 is being rotated continuously in the cutting direction of arrow B in FIG. 2. In an alternate example, the controller may energize the electrode 150 only during a selected arc of rotation, for example, when the electrode 150 is exposed in window 140 while the inner sleeve 128 is being rotated continuously in the cutting direction of arrow B in FIG. 2. In still further examples, the inner sleeve 128 may be rotationally oscillated so that the electrode alternates travel between the directions of arrows A and B in FIG. 2, in which case the controller may continuously energize the electrode or may energize the electrode only while travelling in the direction of arrow B.

In another variation, the system can provide a fluid flow from a fluid source through an inflow pathway (not shown) in the shaver assembly 102 to the working end, for example the annular space between the outer and inner sleeves 125 and 128.

In another variation, the controller 160 may be configured to stop rotation of the inner sleeve 128 and the ceramic body 175 in a selected rotational position relative to the outer sleeve 125. In a selected stationary position, the electrode 150 can be energized with a form of coagulation current for contact coagulation of tissue by the user. The windows or openings 140 and 144 of the outer and inner sleeves 125 and 128, respectively, can be in or out of alignment in the selected rotational position to expose the electrode 150 for such contact coagulation. In another variation, the controller 160 again may be configured to stop rotation of inner sleeve 128 and the ceramic body 175 in a selected rotational position relative to outer sleeve 125 and the stationary electrode 150 can be energized with a form of cutting or ablation current for ablation or contouring of a targeted tissue. Control mechanisms for stopping rotation of the inner sleeve in a selected position may include Hall sensors and microswitches for monitoring rotational speed together with an algorithm for determining the inner sleeve's arc of rotation following stopping current to the motor drive.

Figure 5A:
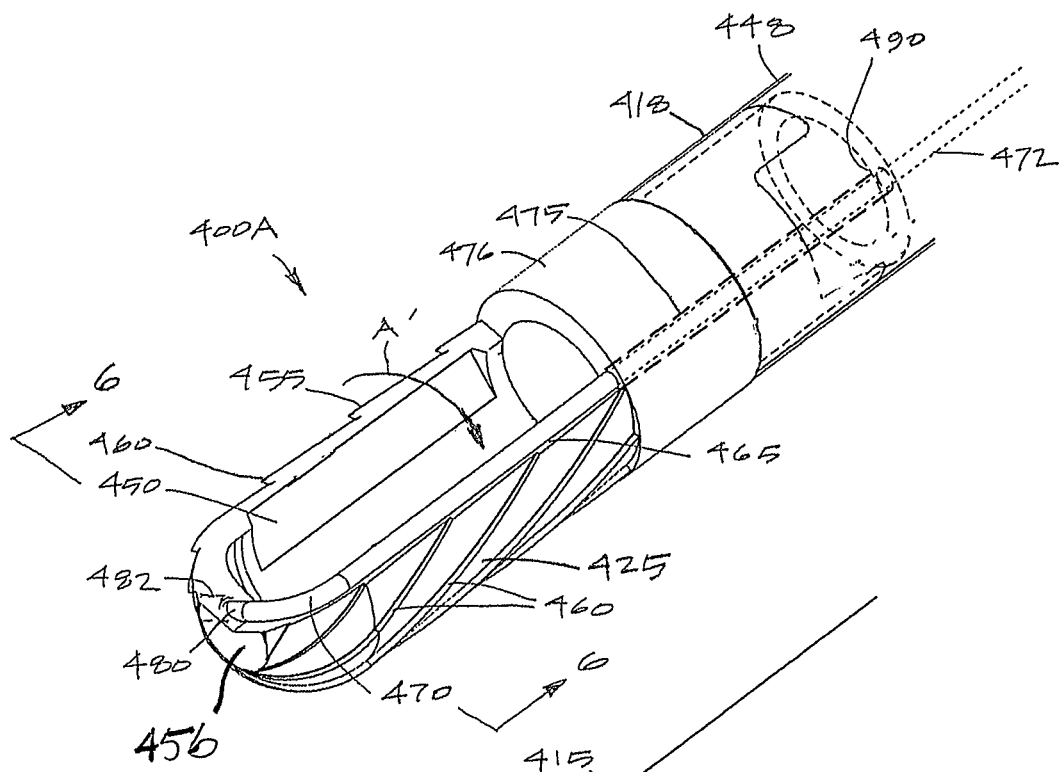
FIG. 5A is a perspective view of the working end of an inner sleeve of another variation of a shaver blade similar to that of FIG. 3A.
Figure 5B:
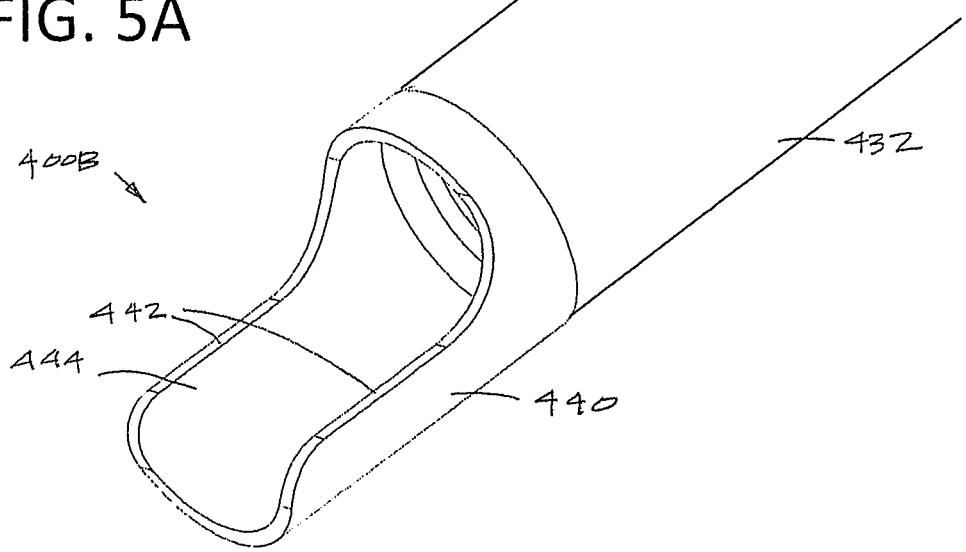
FIG. 5B is a perspective view of the working end of an outer sleeve that carries the inner sleeve of FIG. 5A.

FIGS. 5A and 5B illustrate distal working ends 400A and 400B of inner and outer sleeves 418 and 415 of an alternate embodiment of an arthroscopic shaver blade or assembly constructed in accordance with the principles of the present invention. The distal end 400A of inner sleeve 418 is shown in FIG. 5A, and the distal end 400B of outer sleeve 415 is shown in FIG. 5B. As with prior embodiments, the working end 400A of the inner sleeve comprises a distal portion of a metal sleeve 448 fixedly attached or otherwise coupled to a proximal end of a ceramic body or cutting member 425.

Referring to FIG. 5B, the working end 440B of outer sleeve 415 comprises a distal body or housing 440 coupled (usually fixedly attached) to a distal end of an elongate proximal metal sleeve 432. The housing 440 can be a plastic, metal or ceramic, and in an exemplary embodiment comprises a metal or ceramic material. The ceramic body or cutting member 425 of the inner sleeve 418 is rotatably disposed in a window or opening 444 of the distal housing 440. The window or opening 444 in housing 440 can extend more than half-way (>180°) around the distal end of the ceramic housing 440 and can thus be larger (have a greater exposed area) than window 140 in the outer ceramic body 142 of FIGS. 2 and 3B.

As can be understood from FIGS. 5A-5B, the metal sleeve 448 of working end 400A is rotatably received in a lumen or passageway of the metal sleeve 432 of the working end 400B so that the ceramic body 425 or cutting head can rotate and/or oscillate within the window 444 of the housing 440. The ceramic material of the cutting head 425 is a wear resistant ceramic as described previously.

In a particular embodiment, a wall 442 of distal housing 440 and an outer periphery of cutting member 425 are dimensioned to have a very close tolerance so that the rotation of the cutting member 425 within the window 444 of housing 440 will shear tissue (i.e., have a scissor-like cutting effect) received in window 450 of the ceramic body and windows 444 of the outer sleeve 415 when aligned during rotation (or rotational oscillation) of the cutting member 425 relative to window 444 as indicated by arrow A' in FIG. 5A.

As can be seen in FIG. 5A, the opening or window 450 of ceramic cutting member 425 can extend over a radial angle of from about 20° to 90° of the periphery. In this variation, the window 450 is closed to provide a rounded distal nose 456 of the ceramic cutting member 425. In another variation (not illustrated), the window 450 can be open around the distal nose of the cutting member 425 (thus resembling the open distal end of the housing 440 of the working end 400B). The length of window 450 can range from 2 mm to 10 mm depending on the diameter and design of the working end 400A.

FIG. 5A further shows that the ceramic cutting member 425 has a first edge 455 that is sharp on one side of window 450 similar to the embodiment of FIGS. 3A and 4B. In addition, the ceramic cutting member 425 is configured with a plurality of sharp burr edges 460 which can extend helically, axially, longitudinally or in a cross-hatched configuration around the exterior surface of the cutting member 425, or any combination thereof. The burr edges 460 and the sharp edge 455 of window 450 are adapted to resect soft tissue when rotated or oscillated in an interface with soft tissue wherein the cutting member edges move in scissor-like contact with the lateral side portions 462 of outer sleeve housing 440 as can be understood from FIGS. 5A and 5B. In this variation, the burr edges 460 and sharp window edge 455 also are adapted for cutting bone at high rotational speeds.

Still referring to FIG. 5A, the cutting member 425 may have a second edge 465 around one side of window 450 that carries electrode 470 for electrosurgically cutting soft tissue. In this variation, the electrode 470 may comprise a conductive wire, such as tungsten, that has a shaft portion 472 that extends through a through-hole or bore 475 in the ceramic cutter 425 in proximal body portion 476 of the cutter. The electrode 470 has a distal end 480 that is inserted into another bore 482 in the ceramic cutter 425. The distal end 480 of electrode 470 can be press fit in bore 482 or bonded in said bore.

Figure 6:
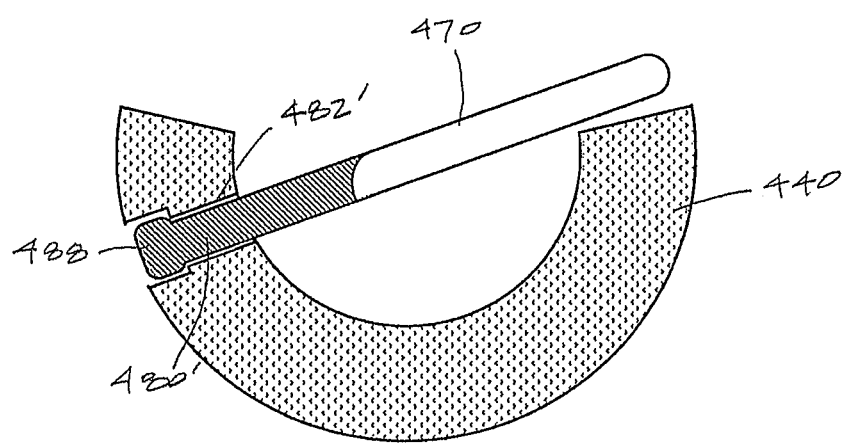
FIG. 6 is a sectional view of the distal end of a ceramic cutting member taken along line 6-6 of FIG. 5A showing a method securing an electrode to a ceramic body.

In another variation, as shown in FIG. 6, a distal end 480' of electrode 470 can extend through a bore 482' in the ceramic body 440, and a weld 488 or crimp can be used to secure the distal end 480' in bore 482'. Referring back to FIG. 5A, the proximal shaft portion 472 of electrode 460 can be covered with an electrically insulating sleeve, as described previously. and extend through the lumen 490 in inner sleeve 418.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A surgical system comprising:
    a sleeve assembly comprising: an outer sleeve having a longitudinal axis and an opening in a distal region thereof;
    an inner sleeve rotationally disposed within said outer sleeve, said inner sleeve having a distal region, a proximal region, and an interior passageway disposed therebetween, wherein a cutting window is formed in a wall of the distal region of the inner sleeve;
    a cutting edge on one side of the cutting window; and
    an electrode on an opposite side of the cutting window; a motor configured to selectively rotate the inner sleeve in first and second rotational directions; a radiofrequency (RF) current source configured to be coupled to the electrode; a controller operatively coupled to the motor and to the RF source; and
    wherein rotating the inner sleeve in a first rotational direction relative to the outer sleeve cuts tissue with the cutting edge and rotating the inner sleeve in a second rotational direction opposite to the first rotational direction cuts tissue with the electrode.

2. The surgical system of claim 1, wherein the controller is configured to selectively operate in a first mode in which the motor rotates the inner sleeve in the first rotational direction with the electrode not energized and in a second mode in which the motor rotates the inner sleeve in the second rotational direction with the RF source delivering a cutting current to the electrode to cut tissue.

3. The surgical system of claim 2 wherein the controller is further configured to selectively operate in a third mode in which the motor drive is stopped with the RF source delivering a cauterizing current to the electrode to coagulate tissue.

4. The surgical system of claim 2 wherein the controller is further configured to selectively operate in a fourth mode in which the motor drive is stopped with the RF source delivering a cutting current to the electrode to cut or ablate tissue.

5. The surgical system of claim 2 wherein the controller is configured to selectively operate in a fifth mode in which the motor rotationally oscillates the inner sleeve relative to the outer sleeve in the first and second rotational directions.

6. The surgical system of claim 1, further comprising a hub at a proximal end of the sleeve assembly, wherein the hub is detachably connected to the motor.

7. The surgical system of claim 1 wherein a proximal portion of the sleeve assembly is configured to be connected to an external fluid source to deliver a fluid through a passageway in the sleeve assembly and release the fluid from a distal region of the sleeve assembly to a tissue interface.

8. The surgical system of claim 1 wherein a proximal portion of the sleeve assembly is configured to be connected to an external vacuum source to draw a vacuum through a passageway in the sleeve assembly to aspirate fluid from a tissue interface at a distal region of the sleeve assembly.

9. The surgical system of claim 1 wherein at least the cutting edge of the inner sleeve comprises a ceramic.

10. The surgical system of claim 9 wherein an entire distal portion of the inner sleeve comprises the ceramic.

11. The surgical system of claim 1, wherein the controller is configured to stop rotation of the inner sleeve in a selected rotational position relative to the outer sleeve.

12. The surgical system of claim 11 wherein the opening in the outer sleeve and the window in the inner sleeve are rotationally aligned in the stopped position.

13. The surgical system of claim 11 wherein the opening in the outer sleeve and the window in the inner sleeve are out of rotational alignment in the stopped position.

14. A tissue treatment device, comprising:
    a sleeve assembly having an outer sleeve and an inner sleeve co-axially received in the outer sleeve; a hub attached to a proximal end of the sleeve assembly;
    a motor attachable to the hub, said motor configured to rotatably drive the inner sleeve relative to the outer sleeve; a radiofrequency (RF) current source configured to be coupled to an electrode; and a controller operatively coupled to the motor and to the RF source
    wherein a window and an opening are formed in distal portions of the inner and outer sleeves, respectively, and wherein the window includes a cutting blade along one axially aligned edge the electrode along a second axially aligned edge; wherein rotating the inner sleeve in a first rotational direction relative to the outer sleeve cuts tissue with the cutting blade and rotating the inner sleeve in a second rotational direction opposite to the first rotational direction cuts tissue with the electrode.

15. An arthroscopic tissue treatment device, comprising:
    a shaft assembly having an outer shaft and an inner shaft received in a passageway of the outer shaft, wherein the inner and outer shafts each have an opening formed in a distal portion thereof;
    a hub coupled to a proximal end of the shaft assembly; and
    a motor attachable to the hub, said motor configured to rotatably drive the inner shaft in first and second rotational directions relative to the outer shaft;
    a cutting blade formed on one side of the opening on the inner shaft; an electrode formed on an opposed side of the opening on the inner shaft; a coupler configured to couple the inner shaft to the motor; a radiofrequency (RF) current source configured to be coupled to the electrode; and a controller operatively coupled to the motor and to the RF source; wherein rotating the inner shaft in the first rotational direction relative to the outer shaft cuts tissue with the cutting blade and rotating the inner shaft in the second rotational direction opposite to the first rotational direction cuts tissue with the electrode.

* * * * *